US006972409B2

(12) United States Patent  (10) Patent No.: US 6,972,409 B2
Sting et al. (45) Date of Patent: *Dec. 6, 2005

(54) MID-INFRARED SPECTROMETER ATTACHMENT TO LIGHT MICROSCOPES

(75) Inventors: Donald W. Sting, New Canaan, CT (US); Robert V. Burch, Sandy Hook, CT (US); John A. Reffner, Stamford, CT (US); Donald K. Wilks, Darien, CT (US)

(73) Assignee: Smiths Detection Inc., Danbury, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 10/744,256

(22) Filed: Dec. 22, 2003

(65) Prior Publication Data

US 2004/0135084 A1    Jul. 15, 2004

Related U.S. Application Data

(63) Continuation of application No. 09/921,461, filed on Aug. 3, 2001, now Pat. No. 6,693,280.

(51) Int. Cl.⁷ .............................................. G01J 5/02
(52) U.S. Cl. ............................................ 250/339.07
(58) Field of Search .................................. 250/339.07

(56) References Cited

U.S. PATENT DOCUMENTS

| | | |
|---|---|---|
| 3,370,502 A | 2/1968 | Wilks, Jr. |
| 4,595,833 A | 6/1986 | Sting |
| 4,758,088 A | 7/1988 | Doyle |
| 4,810,077 A | 3/1989 | Sting |
| 4,843,242 A | 6/1989 | Doyle |
| 4,844,617 A | 7/1989 | Kelderman et al. |
| 4,852,995 A | 8/1989 | Cordier et al. |
| 4,877,960 A | 10/1989 | Messerschmidt et al. |
| 4,878,747 A | 11/1989 | Sting et al. |
| 4,922,104 A | 5/1990 | Eguchi et al. |
| 5,019,715 A | 5/1991 | Sting et al. |
| 5,093,580 A | 3/1992 | Sting |
| 5,160,826 A | 11/1992 | Cohen et al. |

(Continued)

FOREIGN PATENT DOCUMENTS

EP    0426040 A1    5/1991

(Continued)

OTHER PUBLICATIONS

Sales Brochure—Continuum—Printed Feb. 1999.

*Primary Examiner*—Constantine Hannaher
*Assistant Examiner*—Shun Lee
(74) *Attorney, Agent, or Firm*—Foley & Lardner LLP

(57) ABSTRACT

A mid-IR spectrometer attachment performs reflection spectroscopy measurements using commercially available infinity corrected light microscopes without degrading the microscope's performance. The mid-IR spectrometer attachment, which is mounted to and supported by the visible light microscope, introduces infrared radiation into the optical path of the microscope. Radiation from the mid-IR spectrometer source is directed by a trichroic radiation director to a mid-IR objective lens affixed to the microscope nosepiece. The objective lens focuses the radiation on to a subject sample surface in order to acquire either internally or externally reflected infrared spectra by subsequently directing the sample encoded reflected mid-infrared radiation to the radiation director and then to a mid-infrared radiation detection system. The trichroic radiation director can reflect mid-IR, act as a beam splitter for near-IR and transmit visible light to allow the area of mid-IR spectroscopic analysis to be viewed in either visible light or near-IR.

16 Claims, 8 Drawing Sheets

TRICHROIC ELEMENT USED IN A MICROSCOPE, SHOWN FOR VISIBLE, MID IR, AND NEAR IR RADIATION

U.S. PATENT DOCUMENTS

| | | |
|---|---|---|
| 5,166,506 A | 11/1992 | Fiete et al. ............... 250/201.7 |
| 5,200,609 A | 4/1993 | Sting et al. |
| 5,202,744 A | 4/1993 | Louis ........................ 356/73 |
| 5,216,244 A | 6/1993 | Esaki et al. |
| 5,225,678 A | 7/1993 | Messerschmidt |
| 5,278,413 A | 1/1994 | Yamaguchi et al. |
| 5,288,987 A | 2/1994 | Vry et al. |
| 5,434,411 A | 7/1995 | Miyahara et al. |
| 5,552,604 A | 9/1996 | Sting et al. |
| 5,581,085 A | 12/1996 | Reffner et al. |
| 5,703,366 A | 12/1997 | Sting et al. |
| 5,864,139 A | 1/1999 | Reffner et al. ......... 250/339.07 |
| 6,141,100 A | 10/2000 | Burka et al. |
| 6,274,871 B1 | 8/2001 | Dukor et al. ........... 250/339.08 |

FOREIGN PATENT DOCUMENTS

| | | |
|---|---|---|
| EP | 0426040 B1 | 5/1991 |
| EP | 0493777 A2 | 7/1992 |
| JP | 5-164972 | 6/1993 |
| WO | WO95/31711 | 11/1995 |

MID-INFRARED SPECTROMETER ATTACHMENT TO LIGHT MICROSCOPES

PRIORITY CLAIM

This application is a continuation application of application Ser. No. 09/921,461 filed on Aug. 3, 2001, now U.S. Pat. No. 6,693,280, and claims priority thereto.

FIELD OF THE INVENTION

The present invention relates generally to the field of mid-infrared (mid-IR) spectrometry, and more specifically to an attachment to infinity-corrected, commercially available light microscopes to provide the techniques of internal and external reflection infrared microspectrometry.

BACKGROUND OF THE INVENTION

Spectroscopic analysis using radiant energy in the infrared region of the electro-magnetic radiation spectrum is a primary technique for chemical analysis of molecular compounds. The infrared spectral region extends from 0.7 to 250-micrometers, however the mid-IR region is generally considered to cover the region from about 2.5 to about 25-micrometers (or parts thereof), which is commonly used for molecular vibrational spectroscopy. While the primary distinction between near-IR and mid-IR regions is based upon whether the underlying molecular frequencies are fundamental or overtone frequencies, instrument components tend to differ and also be specific by region. There is some overlap however, and specifically mid-IR Fourier transform infrared spectrometers typically cover that part of the near-IR region from 1 to 2.5 micrometers.

This invention defines an attachment apparatus and method for infrared spectroscopic or radiometric analysis of microscopic samples of solids or liquids, including biological materials, combining external or internal reflection spectroscopy with visible light and near-IR radiant energy viewing of microscopic samples by using an attachment to standard commercially available visible light microscopes and commercially available video cameras. The magnification optics for infrared spectral analysis are infrared transmitting objective lenses that are used to focus a beam of radiant energy onto a sample, or sample surface, collect the reflected radiant energy, and present that energy to a detector system for spectral analysis.

Since the introduction of commercial infrared microspectrometers, the advantage of combining the capabilities of a visible-light microscope with an infrared spectrometer has been of great importance. Infrared microscopes, such as those disclosed in U.S. Pat. No. 4,878,747 (the '747 patent) issued to Donald W. Sting and Robert G. Messerschmidt, have been used for an ever-expanding range of applications. These specialized microscopes were attached to commercial Fourier transform infrared (FT-IR) spectrometers. Such microscope/FT-IR systems have been used to detect and identify trace contaminants, to analyze multilayered composites, micro-electronic devices, phase distributions in polymeric materials, inclusions in minerals, abnormal cellular materials, DNA, and numerous other materials.

Heretofore, all known combinations of mid-IR spectrometers and visible light microscopes were composed of (1) a combination of a general purpose laboratory spectrometer and an attachment to the spectrometer having visible light illumination and viewing, or (2) a specially designed integrated instrument combining infrared spectroscopy and visible imaging features. In all cases, the resulting products emphasized the infrared spectroscopy capability, utilizing visible microscopy capabilities as a means to support the infrared spectroscopy capability.

Known special infrared microscope systems and attachments to mid-IR spectrometers have become pervasive even though such systems and attachments are costly and complex. The microscope attachments to laboratory FT-IR spectrometers, described in the '747 patent to Sting and Messerschmidt, among others, have become the standard configurations for infrared microspectroscopy systems. These complex microscope attachments typically provide both transmission and reflection capabilities and use variable remote-image-plane masks to define sample areas for infrared analysis. All of this known art, however, consists of special purpose FT-IR microscopes with specialized optical systems that are appended to large bench-top spectrometers, or fully integrated FT-IR microscope systems using some visible light microscope components. No such systems known use an attachment to visible light microscopes, as is contemplated by our invention.

Our invention provides for the use of both external-reflection and internal-reflection microspectroscopy techniques. Internal-reflection microspectroscopy provides certain advantages over both transmission and external reflection microspectroscopy, particularly in the ability to analyze thick samples. With the introduction of internal-reflection microspectrometry, as shown in U.S. Pat. No. 5,093,580 to Donald W. Sting, and U.S. Pat. No. 5,200,609 to Donald W. Sting and John A. Reffner (also known as attenuated total reflection microspectrometry or micro-ATR) reflection microspectrometry has gained ever-greater importance. Furthermore, our invention extends the capabilities of internal-reflection microspectroscopy by using the unique ATR technology disclosed in U.S. Pat. Nos. 5,703,366 and 5,552,604 issued to Sting and Milosevic to create a novel infinity-corrected ATR objective used for microspectroscopy.

All previous forms of infrared microspectroscopy apparatus were designed from the perspective of the spectroscopist, whereas this invention is designed from the perspective of those using visible light microscopes. Our invention treats the infrared spectroscopy capability as an adjunct to a visible light microscope, and thereby provides extension of the visible microscope's capabilities. It is a primary object of the present invention to provide an FT-IR spectrometer attachment that is easily attached to a commercially available light microscope without compromising any of the available visible light microscope features, options, and capabilities.

SUMMARY OF THE INVENTION

The present invention provides an optical system, apparatus and method to use a mid-IR spectrometer system as an attachment to commercial light microscopes for molecular analysis of materials. In this invention a small spectrometer, in combination with optical, mechanical and electronic components, form an apparatus that can be directly attached to a light microscope for measurement of infrared spectra of microscopic samples or sample domains. Because it can be readily attached directly to existing microscopes, using conventional mechanical connectors that are typically used for microscopes, costs are significantly lower than the current art method of using a dedicated infrared microscope that is attached to a laboratory FT-IR spectrometer. Furthermore, because of the ease of use and accessibility of such low cost infrared spectroscopy capability to material scientists, biologists, and pathologists, as well as others using conventional visible light microscopes, it is expected that significant interdisciplinary benefits will occur.

Using our invention, infrared spectra are acquired using either the external-reflection or the internal-reflection spectroscopy technique. By using reflection spectroscopy techniques, nearly all types of samples can be analyzed. A thin film of material for example, can be mounted on an infrared reflective, but visibly transmissive, substrate such as low-E glass to be analyzed by reflection-absorption, a special case of external-reflection, whereby infrared radiation from the spectrometer is directed onto and through the sample film to the low-E glass substrate, where the radiation is reflected and subsequently passes through the film a second time, whereupon the radiation ultimately is directed to a detector for analysis. An absorption spectrum is thereby acquired, but the measurement was made using the external-reflection technique. For external-reflection spectroscopy, the external-reflection infrared objective lens does not contact the sample, as it must with the ATR objective lens which is used for internal-reflection spectroscopy.

Any thick or thin sample that is placed in contact with the internal-reflection element of an ATR objective lens can result in an ATR spectrum. Because the infrared spectrum of most samples can be measured by using either internally or externally reflected radiation, the infrared spectrometer attachment can provide molecular analyses in a simple and economical manner.

Another object is to use infinity-corrected reflecting objectives and complementary optical components both to direct radiant energy onto a microscopic area and to allow visualization of the magnified image of the specimen and of a highly correlated measure of the mid-IR radiation. The near-IR radiation from the infrared source is used to get this magnified image and correlated measure through an integral video system. Visualization of the mid-IR radiation is achieved by bringing together three distinctly separate ideas in a novel way. First, infrared spectrometers, and specifically mid-IR FT-IR spectrometers, provide a source of infrared radiation that includes some near-IR radiation. Second, commercially available video camera arrays are sensitive to near-IR radiation. Finally, commercially available optical elements are readily made that transmit or reflect radiation differently for different wavelength regions. Using these facts in a novel way caused us to define a new term, a "trichroic' element, meaning an optical element with defined functions in three different wavelength regions. For example, in the preferred embodiment of the mid-IR attachment, the trichroic element largely transmits visible light radiation, it both transmits and reflects near-IR radiation, and it largely reflects mid-IR radiation. The specifics of how the trichroic element is used in conjunction with the preferred embodiment is discussed in detail when describing FIGS. 7 and 8. Using this novel idea and others has allowed us to incorporate the mid-IR spectrometer attachment into infinity-corrected light microscopes to provide unique and significant benefits to the microscopist. In all embodiments, the inclusion of the mid-IR attachment on the microscope maintains a simple optical system without compromising any of the standard features and capabilities of the light microscope.

One embodiment of the invention provides an optical system, which meets the Koehler illumination criterion of focusing the source element of the radiation at the pupil (aperture) of the objective lens. Visible light illumination systems typically meet this criterion, and this embodiment of our invention meets the Koehler illumination criterion for both visible and infrared radiation. To our knowledge, infrared microspectrometer systems have never before been designed to meet the Koehler illumination criterion. This embodiment of our invention, which meets this criterion, we believe, will be of increasing importance to infrared microspectrometry as infrared array detectors become more readily available at affordable prices.

Other objects of this invention will be apparent from the following description, which is provided to enable any person skilled in the art to make and use the invention, and which sets forth the best mode contemplated by the inventors of carrying out their invention. Various modifications to the specific embodiments disclosed herein, within the general principles of the invention as defined herein, will be apparent to those skilled in the art.

DETAILED DESCRIPTION OF THE PREFERRED EMBODIMENT

Figure 1:
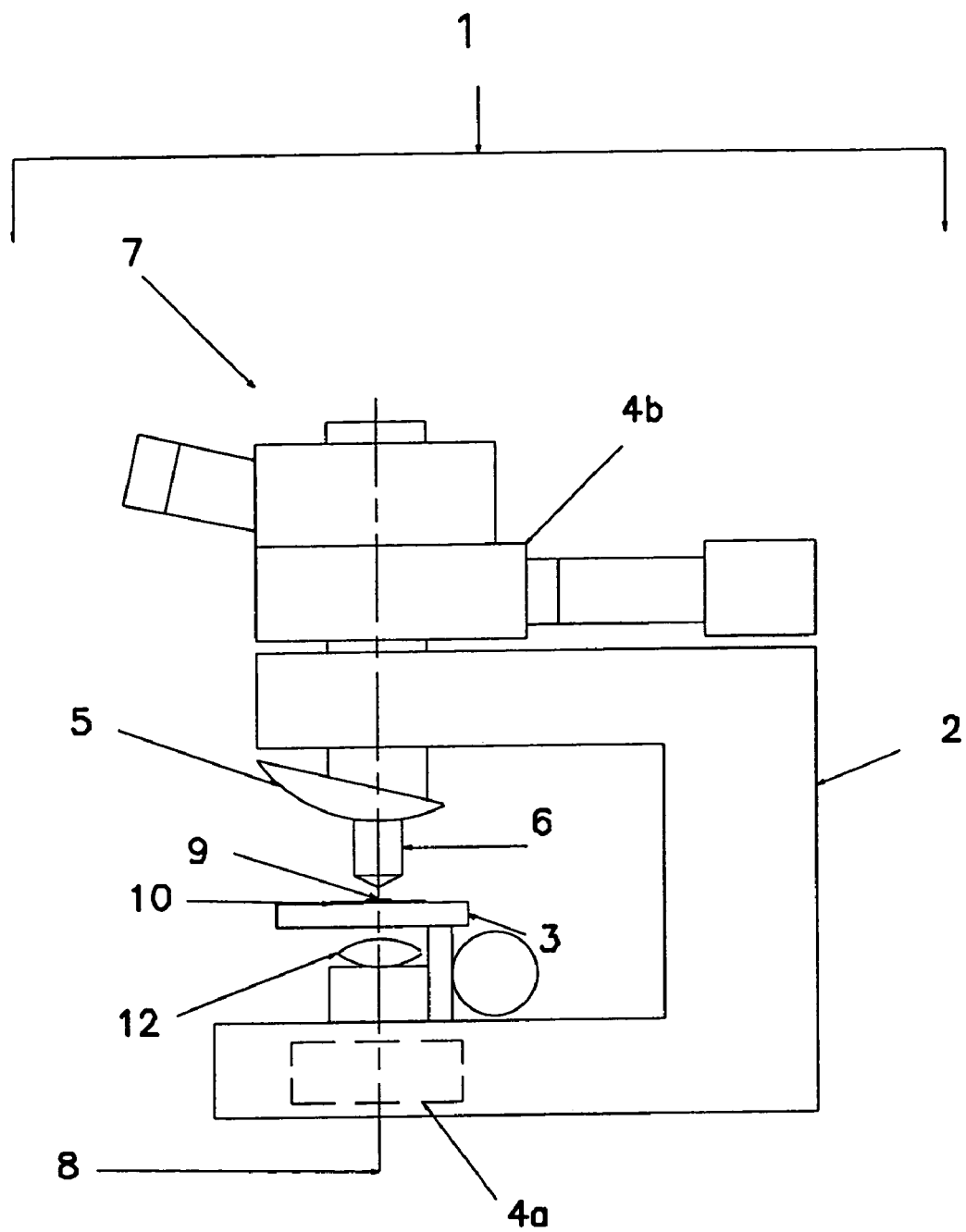
FIG. 1 is a side schematic of a commercially available prior art visible light microscope.

Turning now in more detail to the invention, and initially to FIG. 1, a commercially available infinity corrected visible light microscope is schematically shown as 1. Said microscope is generally composed of a frame 2, a sample support stage 3, transmitted visible light source 4a and/or a reflected visible light source 4b, nosepiece 5, infinity corrected objective lens 6, and visible light viewing means, such as a binocular or trinocular viewer with eyepieces 7. The visible light optics can be used for visual imaging, but mid-IR objective lenses 6 are needed for infrared spectral analysis at wavelengths greater than about 4 micrometers.

All of the optical elements are aligned to the visible light optical path 8 of the microscope 1. A sample 9 is typically placed on a sample substrate 10, which is supported by the sample support stage 3. The sample support stage 3 typically has adjustments to provide for three dimensional spatial movements to place the sample 9 or some attribute of the sample 9 at the focus of the infinity corrected objective lens 6 so that observation by the visible light viewing means 7 is readily effected.

For samples that are transparent or translucent, the transmitted visible light source 4a can be used to provide sample illumination in conjunction with condenser 12. In that case, the visible light beam is transmitted from visible light source 4a along the visible light microscope optical centerline 8 through the condenser 12, the sample substrate 10, then through the sample 9 and the objective lens 6. From objective lens 6, the visible light continues along optical centerline 8 and finally to the visible viewing means 7.

Samples that are visibly opaque might require that the reflected visible light source 4b to be used to illuminate the sample. In that case, visible light from illuminator 4b is introduced along the microscope optical path 8 via a visible beam splitter, which directs light downward to the objective lens 6, which focuses the light onto the surface of the visibly opaque sample 9. Some light is reflected by the surface of sample 9 and collected by the objective lens 6, which collimates the reflected visible light and directs it back to the beamsplitter of visible illuminator 4b, whereby some of the visible light is transmitted through the beamsplitter to the visible light viewing means 7.

In addition, certain samples might require special illumination techniques such as polarized light or radiation of specific frequencies to create florescence or other special visible effects. In such cases, visible light sources 4a or 4b might be readily replaced with such special illumination means, as is known in the art.

Commercially available microscope systems provide for significant flexibility and capabilities, the present invention adds the capability of mid-IR microspectroscopy without degrading those flexibilities and capabilities. The mid-IR spectrometer attachment is mechanically and optically compatible with a plurality of commercial infinity-corrected visible light microscopes.

Figure 2:
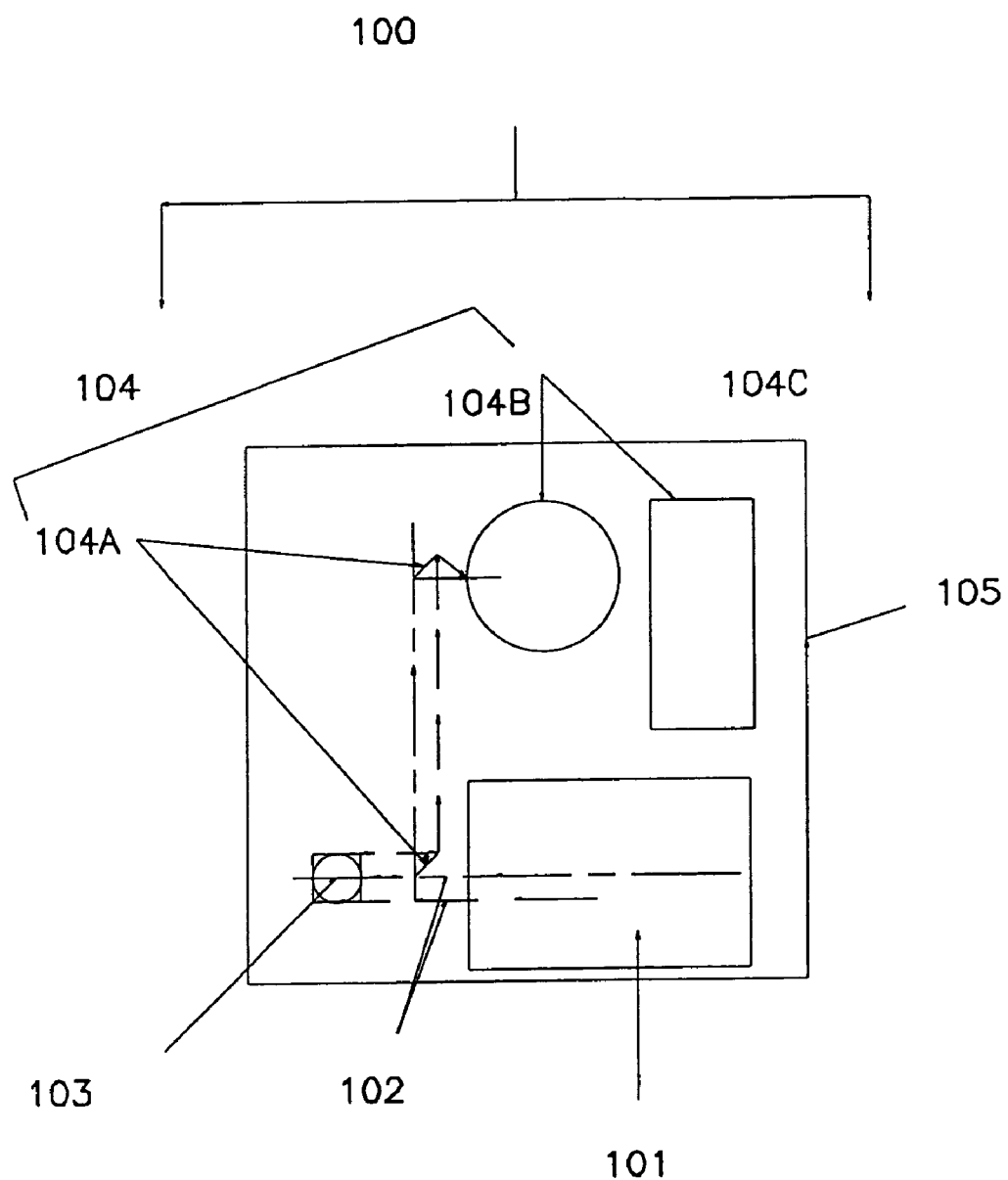
FIG. 2 is a top elevation schematic of the mid-IR attachment of the present invention.

FIG. 2 schematically displays a top view of the preferred embodiment of the present invention, shown generally by 100. The mid-IR spectrometer attachment 100 includes the mid-IR spectrometer source 101, which provides a source of infrared radiation 102 directed toward radiation directing means, or radiation director 103, which is a trichroic element in the preferred embodiment. Radiation director 103 provides the means to couple and align the source of infrared radiation 102 with the visible optical path 8 of the microscope 1, as shown in FIG. 4. Radiation director 103 reflects infrared radiation 102 such that it is aligned with the optical centerline 8 of the microscope 1 for interaction with a sample via an infinity corrected infrared objective lens 6 (see FIG. 4). After interaction with the sample 9, that has been manipulated by the stage 3 (see FIG. 4) adjustments to be at the focus of the infrared objective 6, internally or externally reflected infrared radiation 102 that is now sample encoded is collected by objective lens 6 and returned along the microscope optical path 8, whereby it is reflected a second time by radiation director 103 to the infrared detector system 104. Infrared detector system 104 is composed of directing and focusing mirrors 104a, detector 104b, and detector electronics 104c that are commonly used in the art. Directing and focusing mirrors 104a can be a single mirror or multiple mirrors, largely depending upon the physical space constraints imposed by the size and shapes of microscope components. Detector 104b is typically a high sensitivity cooled MCT detector as is standard practice for infrared microscopes, however, any high sensitivity detector with sufficient broadband width is acceptable. Increasingly, multi-element infrared detectors are being used for infrared microspectroscopy, and we contemplate using multi-element (or multi-pixel) detectors to provide spatial spectroscopic images of samples. Specifically, FIG. 6 discloses a mid-IR. attachment optical configuration intended to have the special benefit of nearly constant infrared radiation density at the sample 9 when using a multi-element detector 104b. Such constant radiation density at the sample 9 minimizes spectral artifacts resulting from different elements (pixels) of the detector being at significantly different radiation levels. All of the mid-IR spectrometer attachment 100 components are affixed to a base plate 105, which cooperates with a cover 106 (see FIG. 3) to provide an enclosure to accommodate a purged environment for the infrared radiation 102.

Figure 3:
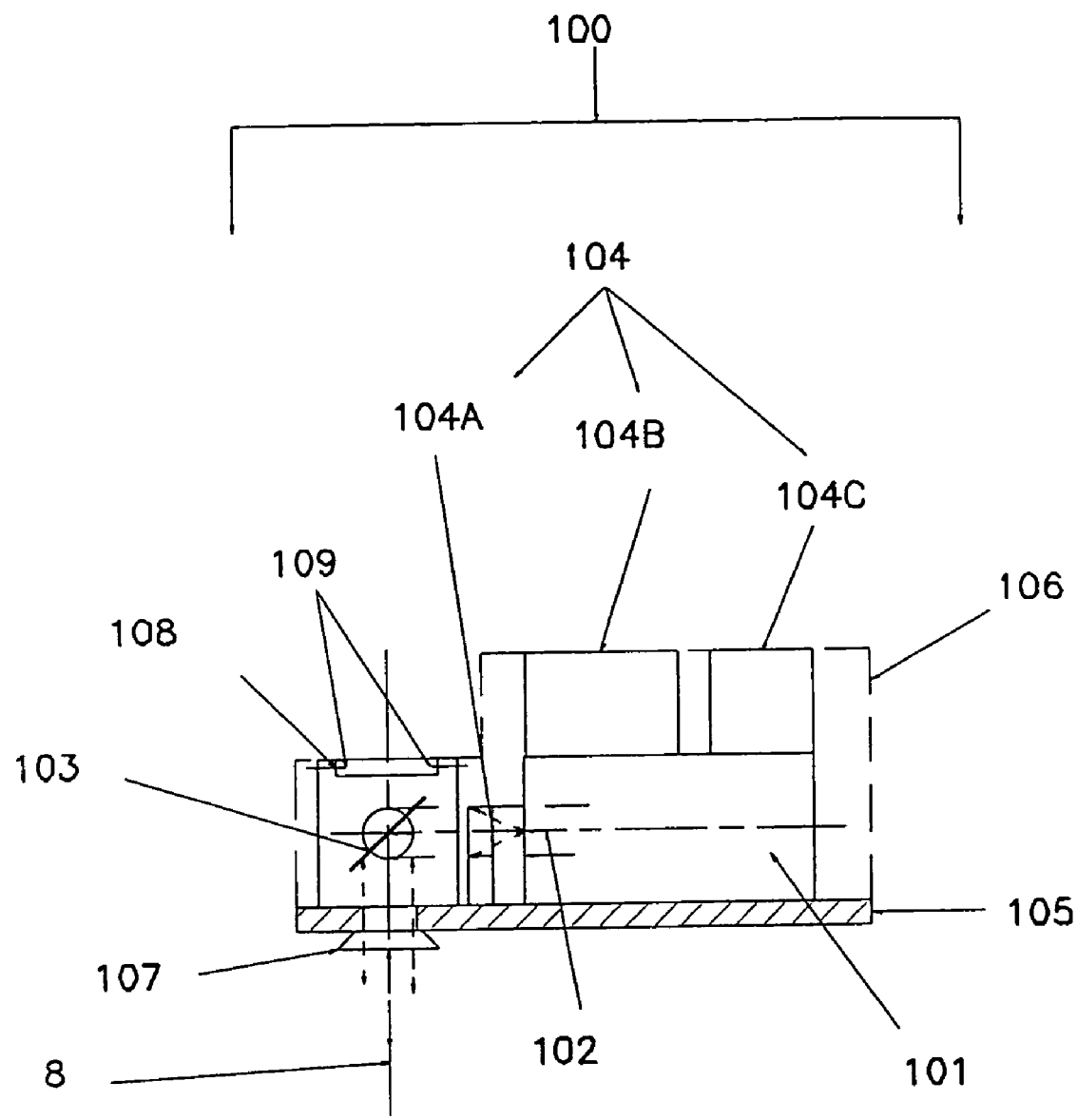
FIG. 3 is a side elevation schematic of the mid-IR attachment shown in FIG. 2.
Figure 4:
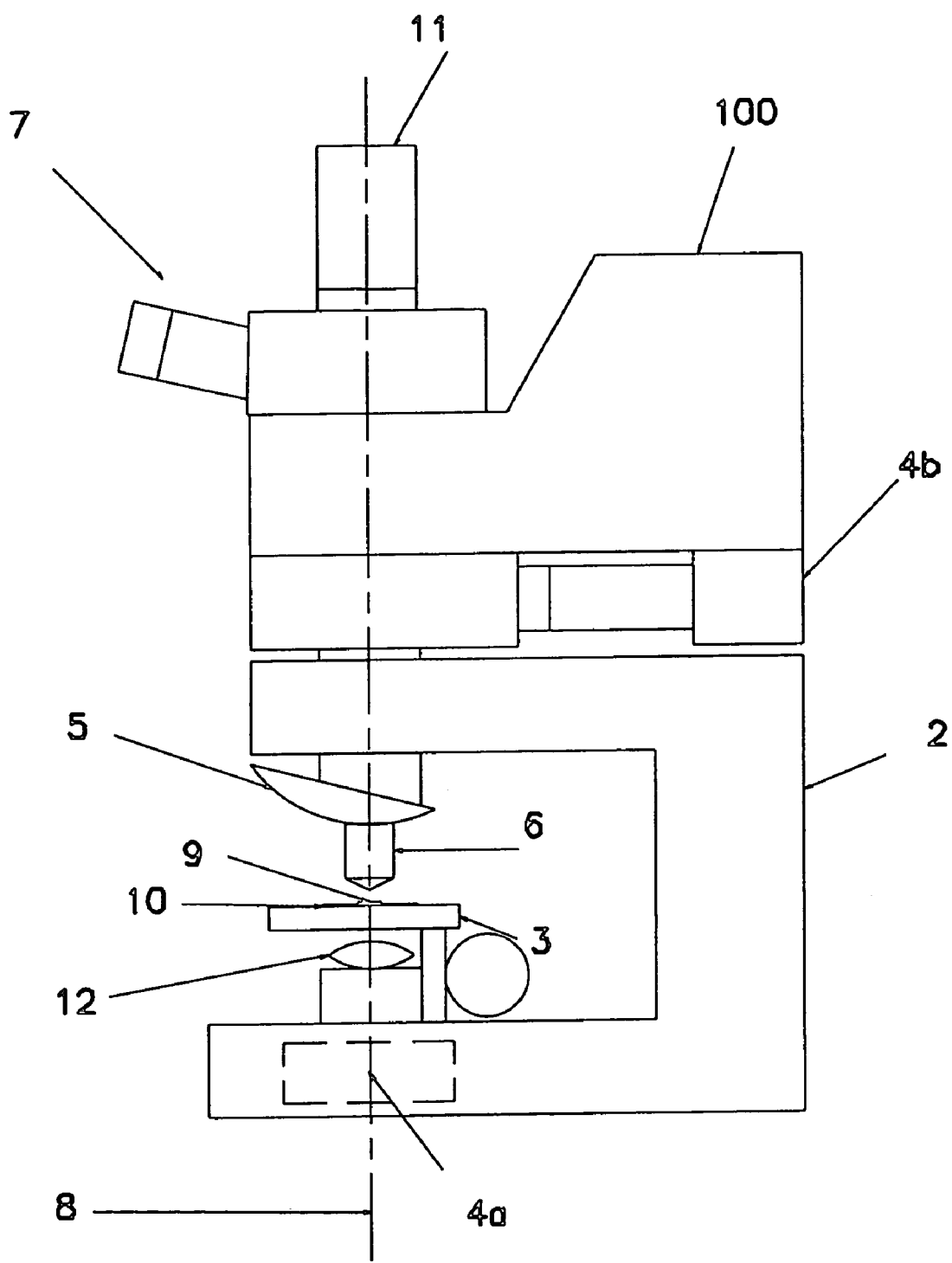
FIG. 4 is a side elevation schematic of the mid-IR attachment as shown in FIGS. 1 and 2 mounted on a commercially available visible light microscope equipped with an objective for internal reflection spectral measurements.

FIG. 3 displays the present invention, showing the various elements, 101 through 106 as they might schematically appear in a side view relative to the microscope optical path 8. Male flange 107 and female flange 108 are complementary to each other and mate to complementary mechanical details on the visible illuminator 4b and the visible viewing means 7 as assembled in FIG. 4. Adjustment screws 109 in female flange detail 108 are used to center the viewing means 7 onto optical centerline 8. Likewise, adjustment screws (not shown) on the visible illuminator 4b provide for alignment of the attachment 100 to the optical centerline 8 of the microscope. Such alignment for concentricity is well known and practiced by those in the art, and is thereby not discussed in detail.

FIG. 4 schematically displays a side view of the mid-IR attachment 100 of the present invention, shown in a usable position with a commercially available infinity corrected visible light microscope 1. As shown, this attachment comprises a small spectrometer that is sized to be mounted to and supported by the visible light microscope. In FIG. 4, both visible light sources 4a and 4b are shown, however the presence of 4a or 4b is dependent only on the visible illumination requirements of the sample being observed and thereby both are not jointly required for the present invention. For many situations, visible illuminator 4b is not required, thereby allowing attachment 100 to be mounted on and connected directly to frame 2. Furthermore, an infinity corrected mid-IR objective lens 6 is shown in the nosepiece 5. It is common practice to use nosepieces that accommodate multiple objective lenses; a single objective lens is shown only for simplicity.

The mid-IR spectrometer attachment 100 is shown in place on a generic commercial light microscope 1 with both a transmitted light illuminator and a reflected light illuminator 4b. Since there are several manufacturers and designs of microscopes, the mechanical fixtures that couple the mid-IR spectrometer attachment 100 to the microscope 1 might vary. The only requirements for the microscope 1 are that it is able to use infinity corrected objectives, and there are no glass elements between the mid-IR spectrometer attachment 100 and the nosepiece 5.

Furthermore, while the reflected light visible source 4b is shown to be below the mid-IR spectrometer attachment 100 of the present invention, with slight modification the reflected visible light source 4b can be placed above the mid-IR spectrometer attachment 100 without compromising the spirit of the invention.

In addition, a video camera 11 is shown, attached to the visible light viewing means 7 to provide for electronic viewing of the sample and/or sample matrix. While such video camera 11 is used in a conventional way to observe a sample, etc., it is furthermore used in a novel, unique way to view the near-IR radiation from the infrared spectrometer source 101. Since the near-IR radiation and the mid-IR radiation are co-mingled as infrared radiation 102, observing the near-IR radiation is a direct measure of the mid-IR radiation, which is not observable by the video camera 11. Commercially available video cameras 11 are typically solid-state video cameras, and some are Charge Coupled Devices, or CCD cameras, although our invention will work with any video camera that is sensitive to near-IR radiation, and/or mid-IR radiation. When used as a mass consumer market video camera, these cameras typically have filters for blocking near-IR radiation that must be removed for our use. An example of such a commercially available video camera, or CCD camera is CBCAmerica Model No. CMLH512-L12 that is sensitive to near-IR radiation. It is used to provide an electronic signal for visual light representation of the near-IR radiation from the infrared spectrometer source. In the absence of visible radiation, we are able to observe the location and extent of the mid-IR spectrometer source radiation by observing the near-IR radiation, which is commingled with the mid-IR radiation. The net effect is that we are able to observe the extent of the mid-IR spectrometer radiation as it interacts with the sample or specific areas of the sample. The trichroic element allows for simultaneous viewing in the near-IR and sample analysis in the mid-IR utilizing infrared energy initially emanating from the same source. To those skilled in the art, this is an extremely important feature since it provides direct observation as to what is being spectroscopically measured.

Figure 5:
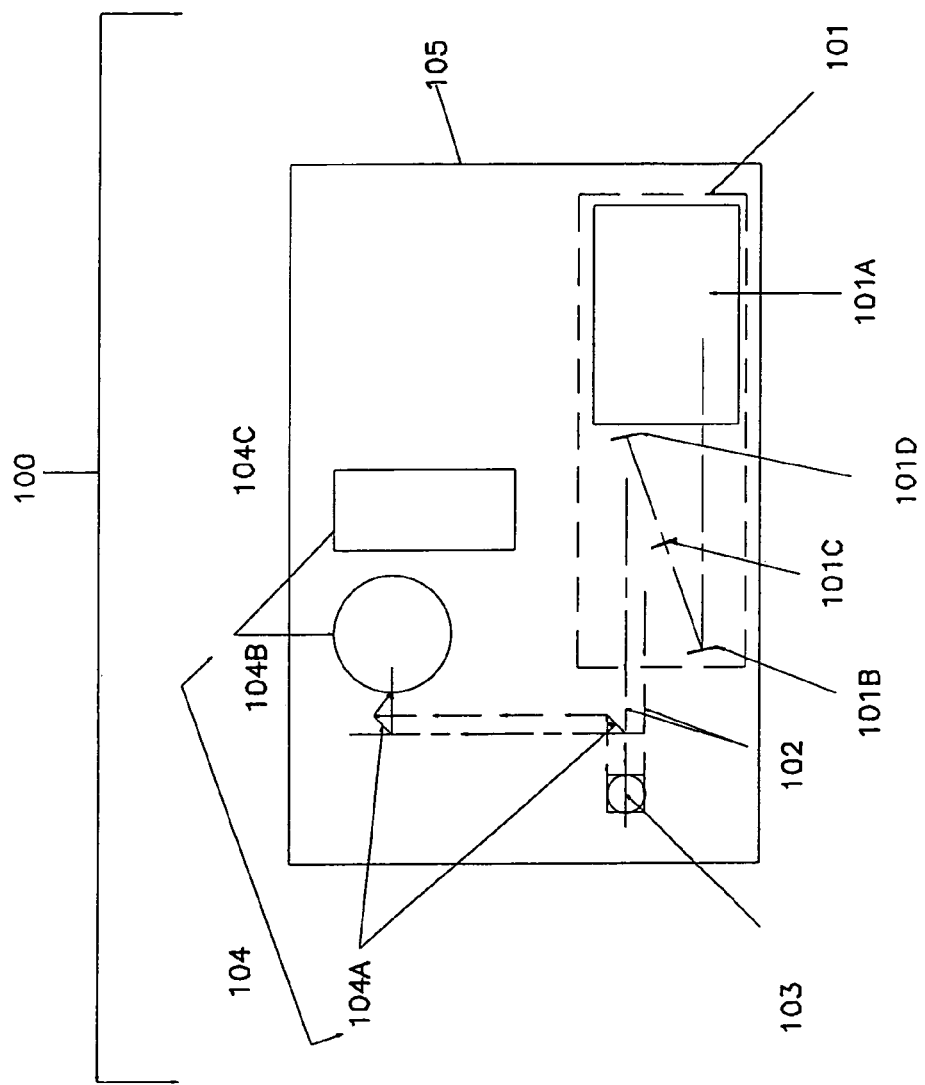
FIG. 5 is a top elevation schematic of the mid-IR attachment of the present invention wherein the mid-IR spectrometer source includes a sample defining mask.

Such direct observation significantly simplifies the analysis process and assures that "what you see is what you analyze". Since the infrared detector 104b will detect all infrared radiation that is in its field of view, it is sometimes necessary to restrict the source of the infrared radiation 102 to be contained within the boundaries of the sample of interest. Such use of sample defining masks is well known in the art and thereby is not described in detail herein. In our invention, in order to achieve more specificity, one sample defining mask 101c, along with optics 101b and 101d are used as shown in FIG. 5 as part of the mid-IR spectrometer source 101. When used in conjunction with a radiation director 103, such as a trichroic element that will be further explained below, and a video camera 11, ample confirmation of "what you see is what you analyze" is provided.

Furthermore, infrared alignment and optical system confirmation are made dramatically easier with the video camera 11. First, the camera 11 is aligned to the microscope 1 with attachment 100, for example as shown in FIG. 4, using visible light means 4a and/or 4b. The radiation directing means 103 and the other optical components of attachment 100 are then adjusted using visible light to grossly align the attachment 100. Then, by switching the visible light source off and leaving the infrared source on, and observing (with the video camera 11) near-IR radiation that is commingled with mid-IR radiation, the attachment 100 is finely adjusted, again using adjustments (not shown) on radiation directing means 103 and the other optical components of attachment 100.

FIG. 5 displays a top elevation schematic of the mid-IR attachment 100 of the present invention, including a sample defining mask 101c, wherein the infrared beam 102 is focused by mirror lens 101b at the sample defining mask 101c and re-collimated by mirror lens 101d and directed to radiation director 103. The mid-IR spectrometer source 101 is herein defined to include mirror lenses 101b and 101d, and sample defining mask 101c.

Figure 6:
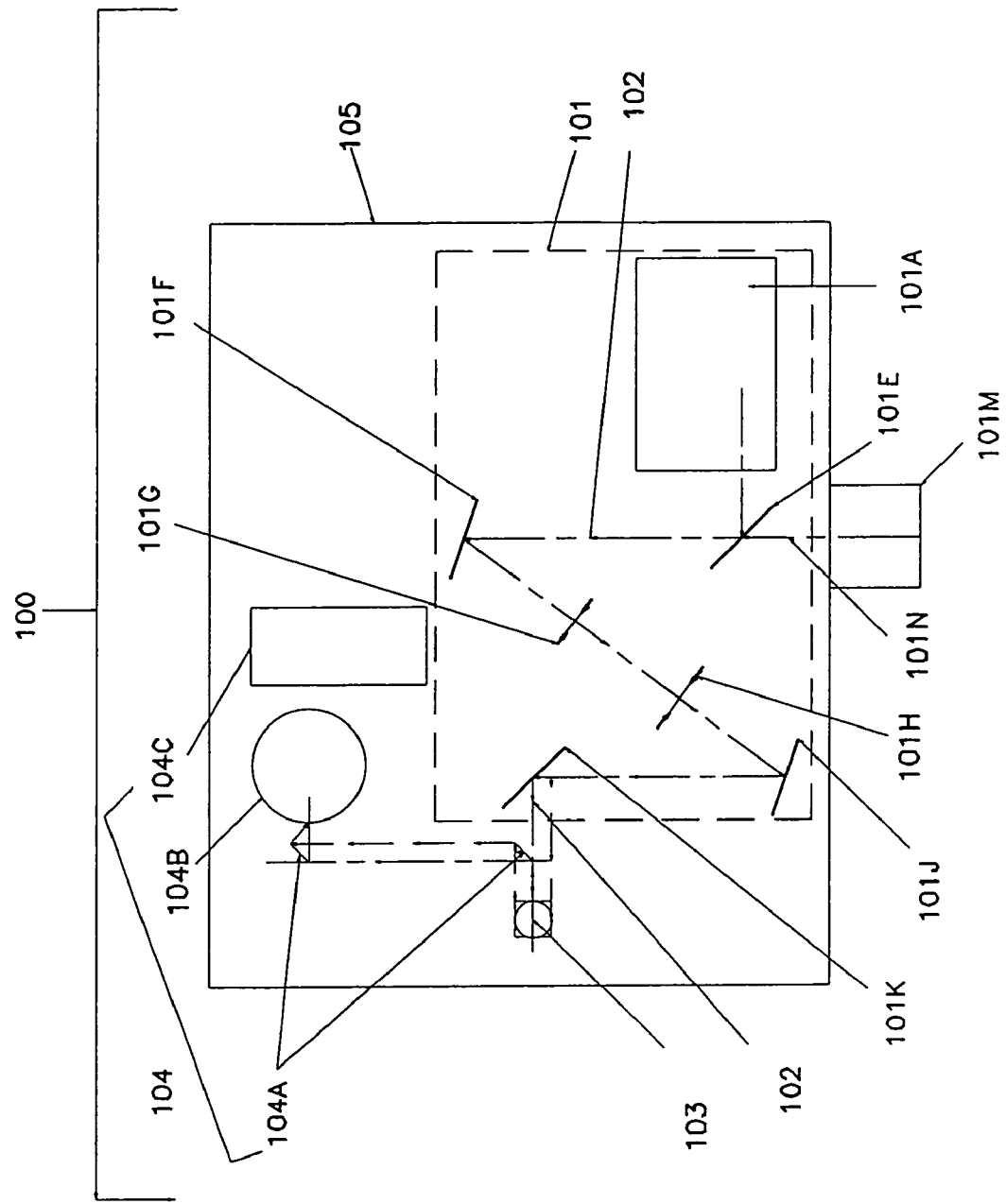
FIG. 6 is a top elevation schematic of the mid-IR attachment of the present invention wherein a visible light illuminator along with sample and aperture defining masks is included.

FIG. 6 displays a top elevation schematic of the mid-IR attachment 100 of the present invention wherein a visible light source 101m, is attached to base plate 105 and is incorporated into the mid-IR attachment 100 of the present invention in order to eliminate the need for and associated cost of a separate visible illumination means 4b. Both the infrared radiation 102 and the visible light beam 101n are subsequently focused, masked twice, and refocused and re-collimated to achieve the criterion of Koehler illumination for both infrared radiation and visible light illumination.

In the figure, infrared radiation 102 and visible light illumination 101n from visible light source 101m are commingled at a trichroic element 101e and made to follow the same optical path 102. The trichroic element 101e is designed to largely reflect mid-IR radiation and near-IR radiation, while largely transmitting visible light 101n.

The commingled visible and infrared radiation, now referred to as 102, is focused by mirror lens 101f to the aperture defining mask 101g, and through sample defining mask 101h, and on to mirror lens 101j which simultaneously creates an image at infinity of all the radiation at sample defining mask 101h and an image of the radiation at mask 101g at the aperture of the infinity corrected objective lens 6, once it has been reflected by flat mirror 101k and radiation director 103. For this configuration, as shown in FIG. 6, trichroic element 103 is a different trichroic element than that of the configurations shown in FIGS. 2 and 5, and is designed to largely reflect mid-IR radiation (reflectivity of around 95%) and to act as a beamsplitter for both near-IR radiation and visible light. This trichroic element design permits the visible light source to be incorporated in the attachment while eliminating the need for a separate vertical visible light illuminator.

The mid-IR spectrometer source 101 in this embodiment is herein defined to include spectrometer 101a, trichroic element 101e, condensing mirror 101f, radiation mask 101g, sample defining mask 101h, lens mirror 101j, directing mirror 101k, visible light source 101m, along with the associated visible light path 101n and the infrared light path 102 commingled with 101n.

In addition to the cost benefit associated with eliminating visible light source 4b, there are benefits associated with microscope alignment and instrument integrity assurance. Furthermore, with the availability of multi-element mid-IR array detectors, it is significant that the Koehler criterion be met in order to insure evenly distributed infrared illumination of the sample and subsequently the detector, for non-absorbing samples.

Figure 7:
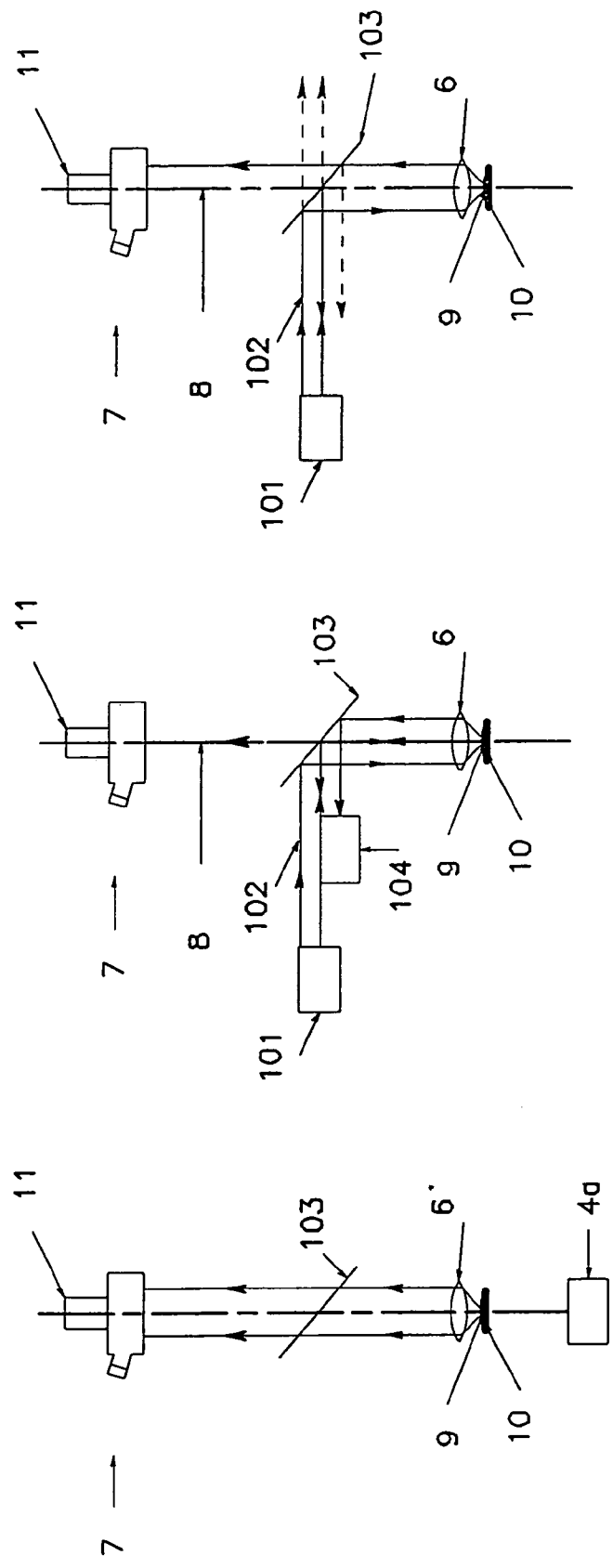
FIGS. 7a, 7b, and 7c are respectively illustrative of how the trichroic element functions for visible light, mid-IR radiation, and near-IR radiation
Figure 8:
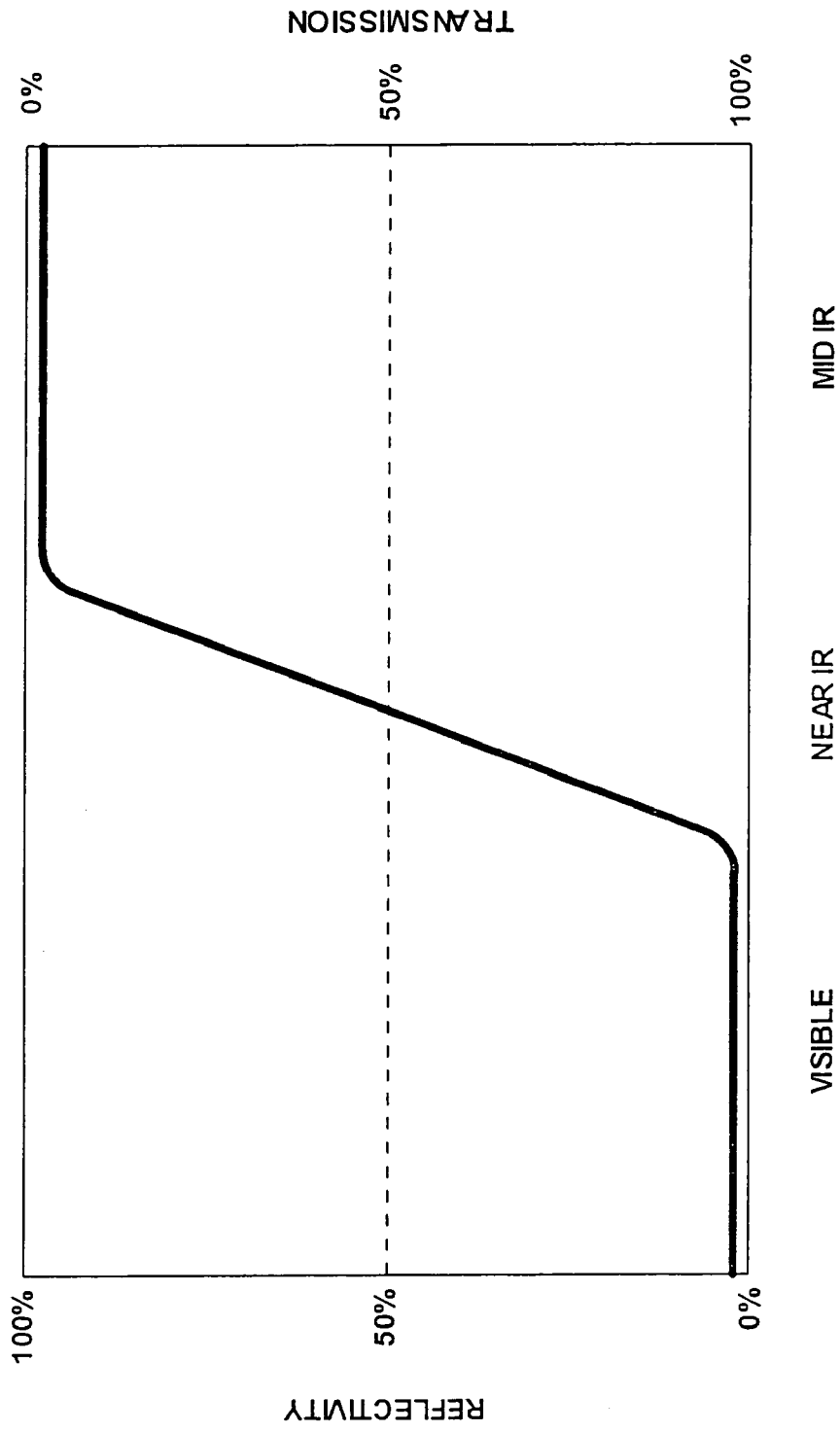
FIG. 8 illustrates reflectance vs. wavelength for visible light, near-IR and mid-IR.

Referring now to FIG. 7, please note the trichroic element 103 is an optical filter element that has three distinct functions. It is substantially transparent to visible light (FIG. 7a) and thereby allows the visible light microscope 1 to operate in a normal fashion (see FIGS. 7 and 8). A sample can be illuminated from either above (see FIG. 4), using visible illuminator 4b, or below, using illuminator 4a, allowing the sample 9 to be observed by the visible light viewing means 7 (see FIG. 7a). For mid-infrared radiation (FIG. 7b), the trichroic element 103 is highly reflective and behaves like a mirror. For example, depending on the composition and thickness of the layers making up the trichroic element 103, reflectivity in the mid-infrared can be as much as 95% or more (see FIG. 8). Radiation 102 from the infrared spectrometer source 101 is reflected by the trichroic element 103 toward the microscopic objective 6. The radiation reflects off the sample 9 or a reflective substrate 10 under the sample 9, back through reflecting objective 6, and back to trichroic element 103. It then makes a second reflection at the trichroic element 103 and is directed to the mid-IR detector system 104, composed of additional optics 104a, detector 104b and detector electronics 104c. In the near infrared the trichroic element 103 behaves like a beamsplitter, as depicted in FIG. 7c. The near infrared radiation from the source 101 travels along the identical path as the mid-infrared radiation, commingled in the infrared radiation 102. When it arrives at the trichroic element 103, some radiation is reflected to objective 6 in the same way as the mid infrared radiation. The rest passes through and is not used. The objective 6 directs radiation to reflect off the sample 9 or a reflective substrate 10 under the sample 9, and back through the reflecting objective 6, and on to trichroic element 103, whereat some of the near-IR radiation is reflected to the infrared detector system 104 and some passes through the trichroic element 103 and on to the visible viewing means 7, which incorporates video camera 11.

The radiation that passes through the trichroic element 103 is detected by video camera 11, which is sensitive to near infrared radiation. The output of the camera can be sent to a monitor for visible viewing. The radiation could be directed to the eyepieces of visible viewing means 7, but it is invisible to the human eye. It should be noted although shown in three separate diagrams, all three modes of operation occur simultaneously. It will be appreciated by those of skill in the art that, depending on the desired reflectance (FIG. 8) for infrared and transmittance for visible and near-IR radiation, the coatings and substrate can be chosen appropriately. For example, reflectance of mid-IR from 80% to 95%, and even up to about 99%, can be achieved. U.S. Pat. No. 5,160,826 to Cohen, et al., which is hereby incorporated by reference in its entirety, discloses a coated window that substantially transmits visible radiation while simultaneously reflecting infrared radiation. Trichroic elements need to be specified by functionality by spectral region and can be ordered from optical component manufacturers such as Spectral Systems of Fishkill, N.Y.

These three functions are novel and important. Transparency of visible light allows normal visible microscopy. Reflectivity in the mid-infrared allows spectroscopic analysis. Since the near-infrared radiation travels virtually the same path as the mid-infrared radiation for optical paths with little or no chromatic aberration, it will illuminate an area that coincides with the area of spectroscopic analysis. Therefore, the camera 11 views the part of the sample 9 that is being analyzed by the mid-infrared radiation. In addition, simultaneous near-infrared and visible viewing, permit precise positioning of the sample 9 on the microscopic stage 3 to select the desired portion of the sample to analyze.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. The invention, in its broader aspects, is not limited to the specific details, the representative apparatus, and illustrative examples shown and described. Accordingly, departures may be made from such details without departing from the spirit or scope of the applicant's general inventive concept.

We claim:

1. A mid-infrared attachment for an infinity-corrected, visible light microscope for spectroscopic analysis of a sample, comprising:
    a source of infrared radiation having mid-IR radiation commingled with at least some near-IR radiation;
    a mid-IR radiation detection system;
    viewing means for near-IR radiation; and
    a radiation director which:
    reflects a majority of the mid-IR radiation from the source of infrared radiation along the optical path of the visible light microscope to the sample as well as reflecting a majority of sample encoded mid-IR radiation returning back from the sample to the mid-IR radiation detection system; and
    splits the near-IR radiation from the source of infrared radiations reflecting a portion of the near-IR radiation along the optical path of the visible light microscope to the sample as well as splitting the sample encoded near-IR radiation returning back from the sample transmitting a portion of the sample encoded near-IR radiation to the viewing means for near-IR radiation;
    wherein said attachment is insertable into the optical path of the microscope and wherein the near-IR radiation is used to observe the area of the sample illumination by the mid-IR radiation.

2. The attachment of claim 1, wherein said radiation director is a single trichroic element, said single trichroic element capable of reflecting a majority of the mid-IR radiation, splitting any near-IR radiation and transmitting a majority of any visible light.

3. The attachment of claim 1 wherein the viewing means for near-IR radiation is a video camera.

4. The attachment of claim 1 in combination with an infinity-corrected light microscope, said microscope including an infinity-corrected mid-IR objective lens.

5. The attachment of claim 4, wherein the microscope includes a frame and a visible light viewing means and the attachment is insertable into the optical path of the microscope between the frame and the visible light viewing means.

6. The attachment of claim 5, wherein said radiation director directs said source of infrared radiation to said objective lens along the optical path of the microscope.

7. The attachment of claim 6, wherein said radiation director directs said source of infrared radiation through said objective lens and onto said sample resulting in reflected sample encoded infrared radiation, said reflected sample coded encoded infrared radiation being directed through said objective lens and to said mid infrared mid-IR radiation detection system.

8. The attachment of claim 7 wherein the attachment is connected to the frame of the microscope.

9. The attachment of claim 7 wherein a video camera is mounted on the attachment for viewing near-IR radiation reflected off the sample.

10. The attachment of claim 1 wherein said radiation director is a trichroic element capable of reflecting a majority of the infrared radiation and splitting any near-IR radiation and any visible light radiation.

11. The attachment of claim 1 wherein said source of infrared radiation is a Fourier transform infrared spectrometer.

12. The attachment of claim 1 wherein the sample is mounted on an infrared reflective substrate for reflection absorption analysis of the sample.

13. The attachment of claim 1 in combination with an infinity-corrected light microscope,
    said microscope including a frame and a visible light viewing means; and
    wherein the source of infrared radiation and the mid-IR radiation detection system of the attachment are housed within a single structure supported by the microscope frame.

14. The attachment of claim 1 further including an optical system operative to direct infrared radiation from said source to said radiation director and from said radiation director to said detection system.

15. The attachment of claim 14 wherein the optical system includes an adjustable sample defining mask between said source and said radiation director.

16. The attachment of claim 14, wherein the mid-IR detection system comprises a mid-IR detector and detector electronics configured to control the mid-IR detector.

* * * * *